United States Patent
Haley

(10) Patent No.: US 9,688,779 B2
(45) Date of Patent: Jun. 27, 2017

(54) TREATING MUCOSAL LESIONS WITH HYALURONAN DELIVERED FROM AN ADHERING TROCHE

(71) Applicant: OraHealth Corporation, Bellevue, WA (US)

(72) Inventor: Jeffrey Haley, Mercer Island, WA (US)

(73) Assignee: OraHealth Corp., Bellevue, WA (US)

( * ) Notice: Subject to any disclaimer, the term of this patent is extended or adjusted under 35 U.S.C. 154(b) by 0 days.

(21) Appl. No.: 14/515,273

(22) Filed: Oct. 15, 2014

(65) Prior Publication Data

US 2015/0104509 A1    Apr. 16, 2015

Related U.S. Application Data

(60) Provisional application No. 61/891,895, filed on Oct. 16, 2013.

(51) Int. Cl.
| | |
|---|---|
| *A61K 9/20* | (2006.01) |
| *C08L 5/08* | (2006.01) |
| *A61K 9/00* | (2006.01) |
| *A61K 31/728* | (2006.01) |
| *C08B 37/08* | (2006.01) |

(52) U.S. Cl.
CPC .......... *C08B 37/0072* (2013.01); *A61K 9/006* (2013.01); *A61K 9/205* (2013.01); *A61K 9/2086* (2013.01); *A61K 31/728* (2013.01); *C08L 5/08* (2013.01)

(58) Field of Classification Search
None
See application file for complete search history.

(56) References Cited

U.S. PATENT DOCUMENTS

| | | | |
|---|---|---|---|
| 6,585,997 B2 * | 7/2003 | Moro | A61K 9/006 424/434 |
| 8,163,716 B1 * | 4/2012 | Smith | 514/62 |
| 2006/0178342 A1 * | 8/2006 | Brown et al. | 514/54 |
| 2006/0194829 A1 * | 8/2006 | Clackson et al. | 514/291 |

(Continued)

FOREIGN PATENT DOCUMENTS

| | | |
|---|---|---|
| WO | WO 0209637 A2 | 2/2002 |
| WO | WO 2007/142973 A1 | 12/2007 |
| WO | WO 2010121081 A1 * | 10/2010 |

(Continued)

OTHER PUBLICATIONS

Nolan et al., "The efficacy of topical hyaluronic acid in the management of oral licen planus", J Oral Pathol Med (2009) 38:299-303.*

(Continued)

*Primary Examiner* — Ernst V Arnold
*Assistant Examiner* — Kyung Sook Chang

(57) ABSTRACT

A troche comprising at least 5 mg hyaluronan, wherein the troche is adherent, and wherein hyaluronan is released from the troche, is used to treat mucositis, including stomatitis, vestibulitis, aphthous ulcerations, lichen planus and Behcet's syndrome. A method for treating or preventing mucositis in a patient is provided, comprising applying to a mucosal surface or a tooth or orthodontic brace of a patient in need thereof an adhering troche comprising at least 5 mg hyaluronan.

16 Claims, 1 Drawing Sheet

(56) References Cited

U.S. PATENT DOCUMENTS

2009/0220497 A1* 9/2009 Brown et al. .............. 424/133.1
2010/0285098 A1* 11/2010 Haley ......................... 424/435

FOREIGN PATENT DOCUMENTS

WO   WO 2011/006263 A1   1/2011
WO   WO 2011/126537 A2   10/2011
WO   WO 2013/123487 A1   8/2013

OTHER PUBLICATIONS

Anti-aging therapeutics, vol. 13 published by American Academy, Ebook Jan. 10, 2012, pp. 1-200 (partial excert is provided).*
Amazon, "HA lozenges (Hyaluronic Acid) 30 prescriptions" [retrieved from http://www.amazon.com/Lozenges-Hyaluronic-Acid-Complementary-Prescriptions/dp/B00Q5KM4C6/ref=sr_1_1?ie=UTF8&qid=1438965173&sr=8-1
&keywords=HA+lozenges+30+Lozenges, last visit Aug. 7, 2015).*
Tipton, "Hydorcolloids", Ebook, part 1, p. 11 (2000).*
Cirillo et al. "A hyaluronic acid-based compound inhibits fibroblast senescence induced by oxidative stress in vitro and prevents oral mucositis in vivo." J of Cell Physiol 2014, DOI 10.1002/jcp.24908.

* cited by examiner

_US 9,688,779 B2_

TREATING MUCOSAL LESIONS WITH HYALURONAN DELIVERED FROM AN ADHERING TROCHE

FIELD OF THE INVENTION

The present invention relates to methods of topically treating mucosal lesions with hyaluronan released from a slowly dissolving adhering troche, including oral wounds as well as inflammatory, ulcerative and painful conditions such as mucositis, stomatitis, vestibulitis, aphthous ulcerations, lichen planus, and Behcet's syndrome.

BACKGROUND OF THE INVENTION

Mucositis is an inflammation of mucous membranes. It typically manifests as an erythematous, burn-like lesion or as random, focal-to-diffuse, ulcerative lesions. Stomatitis is an inflammation of mucous membranes in the mouth. About 20 percent of people suffer from recurrent stomatitis in the form of mouth ulcers, mouth sores, canker sores (aphthous ulcers), denture sores, and sores from cuts or braces.

Stomatitis can occur with or without ulceration, and may be caused or intensified by pharmacological, particularly chemotherapeutic treatments, or by radiotherapy. Stomatitis can range from mild to severe; the patient with severe stomatitis is unable to take anything by mouth, contributing to dehydration and malnutrition.

Many women get oral aphthous ulceration at specific times of the menstrual cycle and some simultaneously get similar ulcers in the genital tract, in particular the vulva and vagina. This is sometimes very severe and can cause retention of urine and require strong painkillers and sedatives. The most severe form is called Behcet's syndrome.

Cancer treatment may have toxic effects on normal cells as well as cancer cells. The gastrointestinal tract, including the mouth, is especially affected because cells in the GI tract are replaced continuously by the body. Mucositis in the mouth (e.g., stomatitis), is one of the most common oral problems occurring after chemotherapy and radiation therapy. Oral mucositis can contribute to oral infections, inability to taste normally, and pain arising from the resulting open sores that can develop.

Oral mucositis frequently also occurs in HIV patients, particularly when associated with Kaposi's sarcoma, in patients affected with non-Hodgkin's lymphoma, in debilitated elderly patients and in patients receiving BRM treatments like interleukin-2, TNF, interferons, lymphokine-activated lymphocytes and the like.

SUMMARY OF THE INVENTION

In one aspect, the disclosure provides a troche comprising at least 5 mg hyaluronan, wherein the troche is adherent, and wherein hyaluronan is released from the troche, thereby treating mucositis. In certain embodiments, the amount of hyaluronan is at least 10 mg or at least 3% hyaluronan. In some embodiments, the hyaluronan has an average molecular weight of at least 1,500,000 daltons.

The troche may be made in a variety of shapes and sizes. In some embodiments, the troche is bilayer, having an adherent layer and a non-adherent layer.

The disclosure also provides a method for treating or preventing mucositis in a patient comprising, applying to a mucosal surface or to a tooth or to an orthodontic brace of a patient in need thereof an adhering troche comprising at least 5 mg hyaluronan. In some embodiments, the adhering troche is applied just before sleeping, in other embodiments, the adhering troche is applied at least once a day every day for prevention. The troche may be used to treat mucositis, including stomatitis or aphthous ulcers, or wherein the mucositis occurs in an oro-pharynx or an oesophagus, or wherein the mucositis occurs in a vagina or a rectum.

The present invention can be more fully explained by reference to the following detailed description and illustrative examples.

DRAWINGS

DETAILED DESCRIPTION

Figure 1:
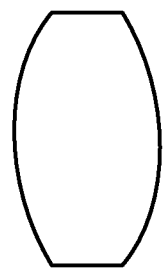
FIG. 1 shows a cross section of an adhering troche in a simple shape.

The present disclosure provides compositions and methods for treating mucositis of a mucosal surface, such as the mouth, vagina, and rectum. Treatment utilizes an adhering troche comprising hyaluronan applied topically close by or in an area exhibiting mucositis. The adherent troche can adhere to gums (keratinized mucosa) or teeth or orthodontic braces as well as to mucosal tissue. Adhering troches for use in the mouth are often called oral adhering discs.

An adhering troche comprises hyaluronan (also called hyaluronic acid or hyaluornate, including sodium hyaluronate), which is an anionic, nonsulfated glycosaminoglycan. The amount of hyaluronan in a troche should be an effective level, a level sufficient to treat mucositis. Typically, a troche comprises at least 5 mg of hyaluronan, or at least 7 mg, or at least 10 mg. In certain embodiments, hyaluronan is at least 2% w/w of the troche ingredients, or at least 3%, or at least 5%, or at least 10%, or at least 20%. When the troche has a bilayer structure and an adhesive other than hyaluronan is used in the adhering layer, the percentage of hyaluronan is at least 2%, or at least 3%, or at least 5%, or at least 10%, or at least 20% of the non-adherent layer.

Typically, hyaluronan comprises disaccharides of D-glucuronic acid and D-N-acetylglucosamine. In vivo, polymers of hyaluronan can range in size from about 5,000 to about 20,000,000 Da. Generally, a higher average molecular weight is used, but may have with a trade-off of cost and uniformity. In some embodiments, hyaluronan has a molecular weight of at least 500,000 Da, or at least $1 \times 10^6$ Da, or at least $1.5 \times 10^6$ Da, or at least $5 \times 10^6$ Da, or at least $10 \times 10^6$ Da. The hyaluronan may be extracted from natural sources such as chickens or bacteria that make hyaluronan. Hyaluronan is available commercially from both of these sources.

An adhering troche may comprise other ingredients, including, for example, one or more adhesives (e.g., acacia gum), one or more binders (e.g., cellulose gum, acacia gum), one or more flavorings (e.g., licorice), one or more medicaments, one or more vitamins, one or more excipients (e.g., salts, buffers), one or more viscous and lubricating substances (e.g., cellulose gum), and one or more adjuvants. In some embodiments only one additional ingredient may be present, in other embodiments, multiple other ingredients may be present. Compositions of other ingredients are well-known in the art.

In certain embodiments, the troche can adhere to gums or teeth, structures attached to teeth (e.g., orthodontic braces), or vaginal, vulval, labial, rectal, anal, or oral mucosal tissue. Hyaluronan itself is muco-adhesive and may comprise all or nearly all of the ingredients of an adhesive troche.

The adhering troche will generally release hyaluronan over a long dissolution time, such as 1-8 hours, for topical application to nearby tissues. Typically, the adhering troche that contains hyaluronan completely dissolves. More precisely, hyaluronan and the binder molecules and other ingredients slowly erode. Some suitable binder molecules are acacia gum and cellulose gum. Optionally, the troche may be made with slowly dissolving hydrocolloids so that that it typically lasts in the mouth for at least ten minutes and up to about six hours. A benefit of delivering hyaluronan with an adhering troche rather than a non-adhering troche (lozenge) is that this allows the troche to be used safely in the mouth while sleeping when saliva flow is lowest and the hyaluronan will linger longest in the mouth. Such a troche may be designed to last 6-8 hours while sleeping.

To ensure that the troche dissolves (erodes) slowly in saliva, a binder that dissolves slowly in saliva is incorporated. Some suitable binders include carrageenan (especially kappa form), xanthan gum, xanthan gum combined with konjac gum, agar, and cellulose gums such as carboxymethylcellulose (CMC), hydroxyproplycellulose (HPC) and hydroxyproplymethylcellulose (HPMC). Other gums similar to those listed, such as locust bean gum which has properties similar to konjac gum, and guar gum are also suitable, as well as starches, such as corn starch or, particularly pregelatinized corn starch.

In one embodiment, a troche comprises hyaluronan, collagen and other binder ingredients. Collagen, which is the organic molecule that makes up skin and the lining of the mouth (a form of skin), tends to adhere very well to itself, making it glutinous, and therefore adheres very well to mucous tissues. An effective and cost effective form of collagen is food grade gelatin, which is made from animal skins.

Figure 2:
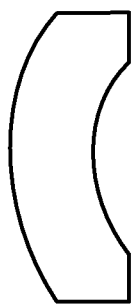
FIG. 2 shows a cross section of an adhering troche in a shape designed to adhere well to gums, a tooth, or an orthodontic brace.
Figure 3:
FIG. 3 shows a cross section of a troche in the form of a patch designed to adhere to mucosal tissue, such as gums, the cheek or lip, vagina, or rectum.

The troche may be formed in a variety of shapes and sizes. A side view of a few exemplary shapes are illustrated in FIGS. 1-3. FIG. 1 shows a troche in the shape of a tablet or lozenge. FIG. 2 shows an exemplary troche that is "dimpled" on one side. FIG. 3 shows a troche in the shape of a thin lentil, often called a patch. This troche is nearly or essentially flat on one side. Many other shapes can be used. When viewed from the top or bottom, troches may be a variety of shapes, and usually will be round or oval. Choice of shape will be based on a number of factors, including ease and cost of manufacturing, surface intended for the troche to adhere, or consumer preference.

The size of a troche will generally also take into account the ease and cost of manufacturing, surface intended for the troche to adhere, or consumer preference. In general, a troche will range from about 5-20 mm or from about 5-18 mm, or from about 7-18 mm, or from about 10-15 mm in at least two dimensions. When the troche is round or nearly round, the size range represents suitable diameters. The thickness of a troche will generally be from 1-10 mm, and more generally from 3-5 mm.

Many suitable manufacturing methods may be used and are well known in the art. One exemplary method of manufacturing troches in the shape of patches is to use gum drop manufacturing equipment, squirting a hydrated mixture heated above the gel melting temperature through nozzles onto a sheet of plastic or coated paper, allowing the troches to cool and gel, and drying the troches. The troches are typically dried until the water activity level is lower than 0.8 to reduce growth of mold or other organisms. The drops are allowed to cool and then the sheets of plastic or coated paper with the drops on them are dried in a drying chamber. The product can be sold still adhered to the plastic or paper, and the user pulls it off the plastic or paper. Other methods for making adherent troches include extrusion of a sheet and then die cutting.

Troches in the form of single layer dissolving mucoadhesive tablets may be made by pressing powders that include mucoadhesive hydrocolloids. In an exemplary method an adhering troche may be made by mixing dry powders consisting of acacia gum (gum arabic) for adhesive and hyaluronan. Hyaluronan itself is adhesive and may comprise all or nearly all of the ingredients at least on an adhesive side. The tablet may be pressed into the shape shown in FIG. 2 for good adhesion to a tooth or gums or orthodontic brace. Such a tablet is usually 8-12 mm in diameter and 80-400 milligrams in weight.

Troches in the form of bi-layer dissolving mucoadhesive tablets for use in the mouth may be made by pressing powders including mucoadhesive hydrocolloids. An exemplary, bilayer adhering troche may be made by mixing dry powders comprising at least 80 percent acacia gum (gum arabic) in the adhesive layer, and may comprise at least 90 percent. The non-adhesive layer may include 20-70% acacia gum as a binder, 5-40% cellulose gum as a binder and moist tissue coating agent, and 2-50% hyaluronan. The tablet may be pressed into two layers which, combined, make the shape shown in FIG. 2, which adheres well to a tooth or gums or orthodontic brace. Such a tablet is usually 9-14 mm in diameter and 120-500 milligrams in weight. It lasts 1-8 hours in the mouth, most commonly 2-4 hours.

A method for treating or preventing mucositis inflammation in a patient comprises administering to a patient in need thereof an effective number of adhering troches each comprising at least 5 mg of hyaluronan. An effective level of use of the adhering troche comprises enough hyaluronan to deliver a dose to mucosa equal to at least 5 mg of hyaluronan spread over nearby tissues in a mouth, or at least 10 mg, or an equal amount per unit area in the vagina or rectum. Optimally, the dissolution time for such a troche is 1 to 8 hours. Because the troches adhere, they will remain in desired locations to treat immediately nearby areas with continuous high concentrations of hyaluronan delivered over time.

The adhering troche may be administered at least once daily every day without end to prevent or reduce the effects of mucositis. In addition to its ordinary meaning, the term treatment encompasses inhibition of progression of symptoms or amelioration of symptoms of inflammation and mucositis. These methods may provide an effective therapeutic or preventive treatment for mucositis and stomatitis of various origins and severity and, more generally, of the lesions of the oro-pharynx cavity and oesophagus, particularly those caused by recurrent aphthous ulceration, dental devices, by radio- or chemotherapy, and by surgery. The troches may be used to treat oral wounds as well as inflammatory, ulcerative and painful conditions such as mucositis, stomatitis, vestibulitis, aphthous ulcerations, lichen planus, and Behcet's syndrome.

Without being bound by a particular mode of action or theory, favorable therapeutic results obtained by the use of the adhering troches comprising hyaluronan are believed to be due to interactions between molecules of hyaluronan with elements of the healing process or the ulceration process.

A typical instruction to users for oral mucositis is to adhere a troche in their mouths, especially near the site of mucositis, as needed. The troches may be supplied in a kit, comprising one or more adherent troche and instructions for use. Troches may be applied continuously, one after another, both during the day and just before sleep, adhering the troche to teeth or gums near the sore so that the hyaluronan as it is released from the troche will coat the sore. Similarly, when mucositis in found vaginally or rectally, a troche may be adhered in the area of mucositis, close to the sore. Tenderness may inhibit users from applying a troche to the sore. As for oral mucositis, troches may be applied sequentially during the day and night. It may be more convenient for the user to apply one just before sleep.

In a particular embodiment in which the adhering troche is administered to the oral cavity, the patient, after applying a dissolving troche, if desired, may refrain from eating or drinking for a certain time, ranging from minutes up to hours.

Such troches were given to test subjects with the above instructions, generating good results in pain reduction while a troche was dissolving and good speeding of healing of aphthous ulcers triggered by bites.

The following examples are presented by way of illustration and not by way of limitation on the scope of the invention.

EXAMPLES

Example 1

A bi-layer troche comprising hyaluronan is manufactured. The adhesive layer comprises at least 80 percent acacia gum (gum arabic) as an adhesive, and may comprise at least 90 percent. The non-adhesive layer includes 20-70% acacia gum as a binder, 5-40% cellulose gum as a binder and moist tissue coating agent, and magnesium stearate as a manufacturing lubricant. The tablet comprises 2-5% hyaluronan. The tablet is pressed into two layers which, combined, make the shape shown in FIG. 2 for good adhesion to a tooth or gums or orthodontic brace. The tablet is 12 mm in diameter and weighs about 100 milligrams in the adhesive layer and 250 milligrams in the non-adhesive layer.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

I claim:

1. A bilayer troche comprising from 5 mg to 250 mg hyaluronan and a mucoadhesive other than hyaluronan, wherein the troche has an adherent layer and a non-adherent layer, wherein the non-adherent layer is a pressed powder that comprises hyaluronan and a lubricating substance, wherein the adherent layer is a pressed powder that comprises the mucoadhesive other than hyaluronan, and wherein, when held in a human mouth, hyaluronan is released from the troche, thereby treating mucositis.

2. The troche of claim 1, wherein the troche comprises from 10 mg to 100 mg hyaluronan.

3. The troche of claim 1, wherein the troche comprises from 2% to 50% hyaluronan.

4. The troche of claim 1, wherein the hyaluronan has an average molecular weight of at least 500,000 daltons.

5. The troche of claim 1, wherein the hyaluronan has an average molecular weight of at least 1,500,000 daltons.

6. A method for treating a mucositis in a patient applying the bilayer troche of claim 1 to a mucosal surface or a tooth or orthodontic brace of the patient in need thereof.

7. The method of claim 6, wherein the hyaluronan has an average molecular weight of at least 500,000 daltons.

8. The method of claim 6, wherein the hyaluronan has an average molecular weight of at least 1,500,000 daltons.

9. The method of claim 6, wherein the adhering troche is applied just before sleeping.

10. The method of claim 6, wherein the adhering troche is applied at least once a day every day for prevention.

11. The method of claim 6, wherein the mucositis is stomatitis or aphthous ulcers.

12. The method of claim 6, wherein the mucositis occurs in an oro-pharynx or an oesophagus.

13. The method of claim 6, wherein the mucositis occurs in a vagina, vulva, or rectum.

14. The troche of claim 1, wherein the non-adherent layer comprises no more than 50% hyaluronan.

15. The troche of claim 1, wherein the lubricating substance is cellulose gum.

16. The troche of claim 1, wherein the lubricating substance is magnesium stearate.

* * * * *